United States Patent [19]

Tersteegen et al.

[11] 4,144,884
[45] Mar. 20, 1979

[54] DOUBLE LUMEN CATHETER

[76] Inventors: Bernd J. W. Tersteegen; Günther Van Endert, both of Kreuzstrasse 19, D-4000 Dusseldorf 1, Fed. Rep. of Germany

[21] Appl. No.: 778,720

[22] Filed: Mar. 17, 1977

[30] Foreign Application Priority Data

Mar. 29, 1976 [DE] Fed. Rep. of Germany ....... 2613281

[51] Int. Cl.$^2$ .............................................. A61M 5/00
[52] U.S. Cl. .................................. 128/214.4; 128/221; 128/347
[58] Field of Search ............ 128/214 R, 214.2, 214.4, 128/221, 240, 347, 348, DIG. 16

[56] References Cited

U.S. PATENT DOCUMENTS

| 1,087,845 | 2/1914 | Stevens | 128/221 |
| 3,662,754 | 5/1972 | Halloran | 128/221 |
| 4,000,739 | 1/1977 | Stevens | 128/214.4 |
| 4,014,333 | 3/1977 | McIntyre | 128/240 |
| 4,037,599 | 7/1977 | Raulerson | 128/214.4 |

FOREIGN PATENT DOCUMENTS 265972 10/1913 Fed. Rep. of Germany ........ 128/214.4

Primary Examiner—Dalton L. Truluck

[57] ABSTRACT

A double lumened catheter defined by inner and outer cannulas having spaced apart walls defining a fluid passageway therebetween. The outer cannula is sharpened at its outer end for ease in puncturing a blood vessel. The inner cannula is extendible past the sharpened end of the outer cannula and is bent at an angle toward the inner wall of the outer cannula. Engagement of the bent portion of the inner cannula with the sharpened front end of the outer cannula's inner wall prevents damage to the blood vessel after insertion of the double lumened catheter thereinto. After insertion, blood may be dialyzed by with-drawing blood through the space between the cannulas and returned via the inner cannula.

8 Claims, 1 Drawing Figure

U.S. Patent  Mar. 20, 1979  4,144,884
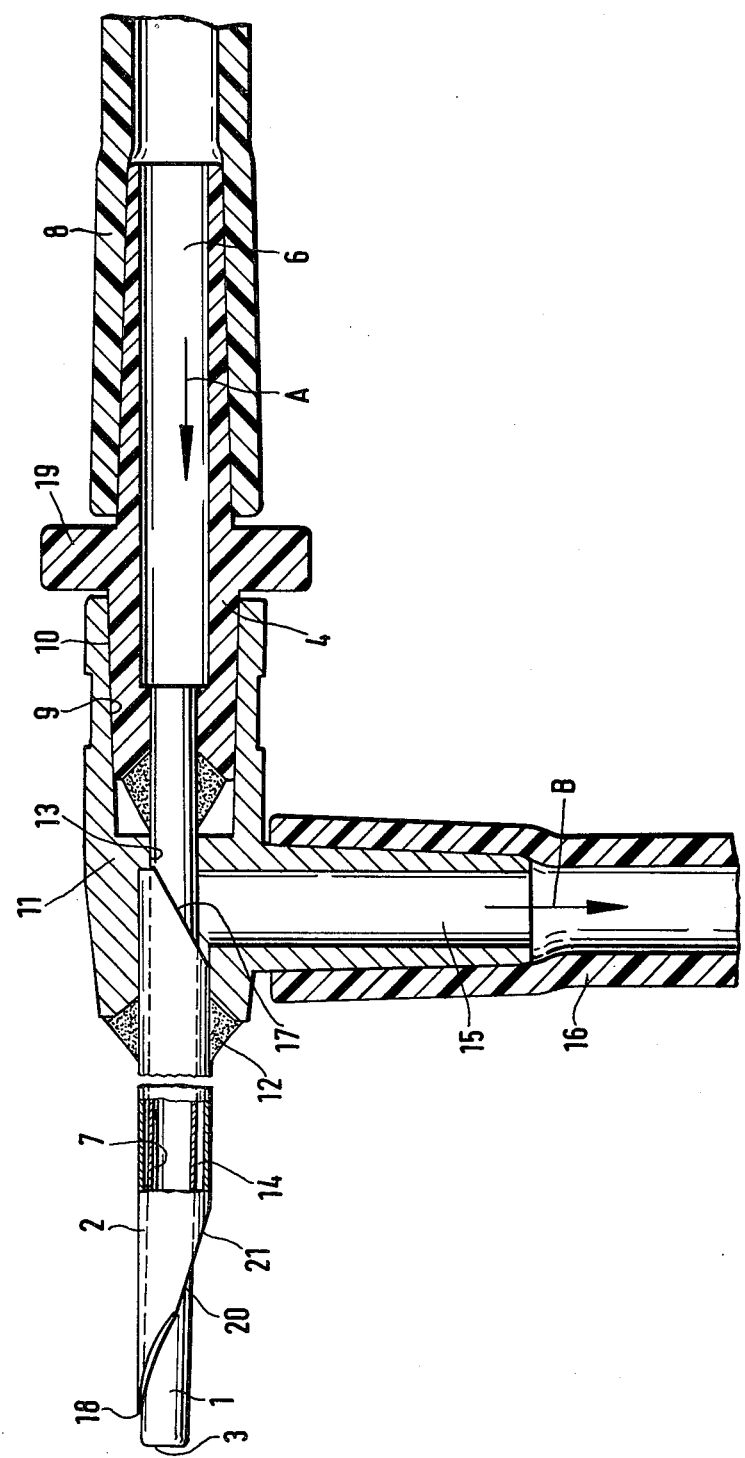

DOUBLE LUMEN CATHETER

The invention concerns a double lumen catheter, in particular for providing blood vessel access in extra-corporal hemodialysis, and having separate ducts for blood streams flowing into and out of the body.

Extra-corporal hemodialysis is a process for treating chronic kidney failure in its final stage, which because of its life-saving effectiveness has gained general acceptance. In this process, the patient's blood is passed over a dialysing membrane for several hours during treatment at a rate of about 150 to 250 ml/per min., and is thereafter immediately returned to the patient. Exchange of uremic poisons from the blood takes place across the membrane into a dialysing solution flowing on the other side of the dialysing membrane. In order to maintain life, it is necessary that the extra-corporal hemodialysis be carried out about two or three times weekly, each time for an average period of six hours. One problem of extra-corporal hemodialysis is the problem of access to the blood vessel. For this, the so-called Scribner-shunt has become known. In this case, an operation is performed to interconnect an artery and a nearby vein (generally in the lower arm of the patient) by a plastic tube. The plastic tube is inserted through the skin after tying of the blood vessels. The outer portion of the tube is divided and connected by a coupling part. The blood rushes constantly at a high speed through this artificial short circuit (arterial-venous shunt) during the treatment intermissions, because of the considerable pressure difference between the artery and the vein. In order to accomplish extra-corporal hemodialysis, the arterial and venous parts are disconnected and connected to the artificial kidney, that is the arterial part is connected to the entry and the venous part is connected to the output of the dialyzer. The tubes are disconnected from the artificial kidney after treatment and remain coupled to each other until the next treatment.

In this type of vessel access there exists the drawback that new parts of the blood vessel must be continuously opened up, since the operational life of this type of blood vessel connection is limited due to typical complications, such as the formation of coagulation at the connection of the plastic tubes and in the blood vessels into which they are connected, as well as the life-endangering general and local infections caused by bacteria entering into the body through the skin at the point where the plastic tubes pass through the skin.

In providing access to a blood vessel, it has further become known to directly join together an artery and a vein usually in the lower arm, by sewing together an artery and vein in an operation. Because of the considerably higher blood pressure in the artery relative to that in the vein, the wall structure of the substantially weaker vein will expand considerably so that its cross section assumes a multiple of its original size until the vein wall becomes adapted to the higher pressure and the far larger blood quantity flowing through it per time unit. Such an "arterialized" vein can then, in favorable instances over some years be punctured by a larger lumen cannula (about 1.6 to 2 mm inside diameter) for the blood inflow and the blood return. The cannula is removed after treatment. The punctures heal in natural fashion. This type of vessel access has the drawback that the optimum anatomical and biological development of the so-called "cimino-bresciafistula" requires a time period of several weeks to some months. Moreover, the anatomical and functional develpment is not always good, and each scar formed after a puncture leads to a weakening of the blood vessel wall. It is therefore more advantageous if the connection between the patient and the artificial kidney is made by a single catheter only.

It has already been suggested to connect an ancillary device having a valve function in series with a single cannula. This arrangement works in such a way that the blood is alternately aspirated through the cannula, then the valve being switched, and the blood returning through the same cannula. The so-called single needle technique requires a considerable additional equipment and increased cost.

In addition to this, it is also known to couple an artificial kidney to a patient with only one puncture. In this double lumen catheter, the inner duct of the inner cannula is provided for the inflowing blood stream an annular duct between the inner cannula and an outer cannula surrounding the inner cannula is provided for the outflowing blood stream. The internal cannula of this double lumen catheter is sharply honed to facilitate puncture of the blood vessel. For this reason, the front end of the inner cannula projects considerably farther than the front end of the outer cannula. This leads to a relatively high resistance to flow in the inner duct of the inner cannula used for the blood return. The front end of the outer cannula tapers conically toward the outer wall of the inner cannula and has three apertures as aspiration openings directly behind this conical section. The drawback of this catheter is that the configuration of the aspiration openings leads to a high resistance to suction, a turbulent flow and dead spaces in the most forward portion of the annular duct between the inner and outer cannulue, so that this known cannula promotes coagulation and closure of the annular duct. Furthermore, the interrupted surface of the outer cannula is undesirable during insertion of the double lumen catheter into the blood vessel.

The present invention has provided a double lumen catheter which avoids the drawbacks of the known double lumen catheter as well as the other techniques mentioned above.

The present invention provides a double lumen catheter having an outer cannula that is sharply honed at its front end to facilitate puncture of the blood vessel. The double lumen catheter includes an inner cannula that is slidably mounted within the outer cannula, and the aspiration opening for the annular duct between the inner and outer cannulue is an annular passage at the front end of the annular duct. During puncturing of the blood vessel, in accordance with the present invention the inner cannula is retracted into the outer cannula. When the front end of the outer cannula is within the blood vessel the inner cannula is pushed forward. Since the aspiration opening has the form of an annular passage, the aspiration opening wil not increase the resistance to suction. In addition, there is no turbulent flow in the aspiration opening and there is no dead space in the most forward portion of the annular duct.

In accordance with another aspect of the present invention, the rear end of the outer cannula may be provided with a Y or T shaped coupling device having a fixed step. The coupling device includes a guiding aperture tightly surrounding the inner cannula and a coupling end communicating with the annular duct, with tube being affixed to the coupling end to conduct the outflowing blood stream from the double lumen catheter.

In accordance with yet another aspect of the present invention, the step of the coupling device is formed at its free end by a guide sleeve having an outwardly tapering conically shaped guide surface. The inner cannula is fixed to a coupling part having an externally tapered end slidably received within the guide sleeve of the coupling device. The taper on the end of the coupling part corresponds to the taper of the guide sleeve, and when the tapered surfaces are in engagement with one another, the front end of the inner cannula protrudes at least to the front face end of the outer cannula. With the tapered surfaces in engagement with one another, the position of the inner cannula is fixed with respect to the outer cannula and the possible aspiration of air is prevented.

In accordance with still another aspect of the present invention, the coupling part is provided with a flange type protrusion to facilitate manual manupulation of the coupling part and inner cannula.

In order to prevent the sharply honed point of the outer cannula from injuring the blood vessel in accordance with a further aspect of the present invention the front end range of the inner cannula is bent in the direction to the inner wall of the outer cannula. This has the inner wall of the sharply honed end of the outer cannula resting with a light pressure against the inner cannula, which prevents the sharply honed front face end of the outer cannula from cutting the vessel after the outer cannula has punctured the vessel and the inner cannula has been pushed forward.

This invention will next be explained in greater detail by reference to the embodiment shown in the drawing.

BRIEF DESCRIPTION OF THE DRAWING

The single FIGURE is a broken cross-sectional view of a double lumen catheter in accordance with the present invention, with the inner cannula in an extended position.

DETAILED DESCRIPTION

The double lumen catheter has a tubularly inner cannula 1 and a tubular outer cannula 2 coaxial with it. The inner cannula has an open front end 3 disposed generally perpendicularly to the axis of the inner cannula. The rear end of the inner cannula 1 is connected to a plastic coupling part 4 and is fixed to the coupling part by means of glue or another sealing material. The couplng part 4 has an inner duct 6 which communicates with the inner duct 7 of the inner cannula 1. A coupling tube 8 is fitted onto the rear end of the coupling part 4, and the inflowing blood stream passes through tube 8 and ducts 6 and 7 in the direction of arrow A. The forward end 10 of the coupling part 4 is externally tapered and generally frusto-conically shaped and in the position shown, is seated within a corresponding outwardly tapered conically shaped guide sleeve 9 of a coupling device 11. The outer cannula 2 is fitted within the forward end of coupling device 11, and affixed to it by means of glue or another sealing material 12. The coupling device 11 which is generally T-shaped as shown in the drawing, has a guiding aperture 13 tightly surrounding the inner cannula 1. An annular passage 14 is formed between the outer wall of the inner cannula 1 and the inner wall of the outer cannula 2 and communicates with a perpendicularly disposed inner duct 15 of the coupling device 11. A coupling tube 16 is fitted over the lower end of the coupling device, and the outflowing blood stream flows in the direction of arrow B through passage 14, duct 15 and tube 16. The outer cannula 2 has a slanted end 17 to permit an undisturbed passage of the blood from the annular passage 14 into the duct 15. The leading end 18 of the outer cannula is sharply honed to facilitate puncturing.

In order to carry out the puncture, the inner cannula 1 is grasped manually by a flange type protrusion 19 on coupling part 4 and is moved to the right with respect to the outer cannula 2 from the position shown in the drawing until the front end 3 of the inner cannula 1 is positioned rearwardly of the eye 21 of the sharply honed point 18. In this position, the tapered surfaces 9 and 10 separate and the inner cannula 1 has slid to the right through the guiding aperture 13, whch effects a seal against the exit of blood and the entry of air because of its tight sealing engagement with the outer wall of the inner cannula. The catheter is then introduced into the blood vessel of the patient in the usual manner. Once the outer cannula 2 with its sharply honed point 18 is in the blood vessel, the inner cannula 1 is pushed forwardly into the position shown in the drawing. This causes a seating and sealing relationship by virtue of the tapered surfaces 9 and 10 engaging one another whereby the position of the inner cannula 1 is fixed with respect to the outer cannula 2 thereby preventing aspiration of air.

As can be seen from the drawing, the free end portion of the inner cannula 1 is bent at an angle in the direction of the inside wall of the outer cannula. In the position shown in the FIGURE the inside of the sharply honed point exerts a light pressure against the outer surface of the inner cannula. This prevents the sharply honed point 18 from causing injuries to the blood vessel after its introduction therein. The annular duct 14 is formed continuously right to the front end of the outer cannula 2, so that there is no need for a special formation of an aspiration opening, such as drilled holes or the like, and the aspiration opening of the annular duct 14 is therefore a non-constricted gap, thus permitting unimpeded flow.

In another embodiment of the invention not shown in the drawing, the bevel formed from honing the front face end of the outer cannula 2 is arranged with respect to the T-shaped coupling device 11 such that the top view of the bevel represents an oval when the part of the coupling device 11 showing the inside duct 15 runs in the direction of the small diameter of the oval. Thus, since the double lumen catheter is generally introduced with the honed point of the outer cannula downward, this embodiment permits turning the catheter 180° so that the end facing away from the beveled point protrudes farther into the blood vessel. This is of special importance when the inner and outer cannulue have been made as short as possible to reduce the resistance to flow, for instance.

Numerous clinical tests have shown that the double lumen catheter in accordance with the present invention can be used on all patients without problems having no excessive and unbearable over or under pressures at comparable blood quantities per time unit in comparison to the customary two-cannula technique. Coagulation inside the cannulue, which would have led to a closure of the blood canal, could not be observed. Despite the relatively large diameter of the puncturing instrument, no after-bleeding was observed either fron the punctured vessel.

We claim:

1. A double lumen catheter for use in extra-corporal dialysis, which comprises ducts for blood streams flowing into and respectively out of the body, an inner cannula providing an inner duct, an outer cannula surrounding the inner cannula and providing between the inner cannula and the outer cannula an outer duct, said outer cannula being disposed in co-axial relationship with respect to said inner cannula, a front end of the outer cannula being inclined obliquely to the longitudinal cannula axis and sharply ground to facilitate puncture of a blood vessel, the front end portion of the inner cannula being bent with respect to the longitudinal cannula axis, the magnitude of the bend of said front end portion of said inner cannula being sufficient to locate the leading end of said front end portion in a position bearing against an inner wall of said outer cannula, and means mounting said inner cannula for axial movement relative to said outer cannula from (1) a withdrawn insertion position wherein the front end of the inner cannula is positioned inwardly of the front end of the outer cannula so that the sharply ground front end of the outer cannula can puncture a blood vessel, (2) to an extended operative position wherein the front end of the inner cannula extends to least to the front end of the outer cannula, whereby engagement between the sharply ground front end of the outer cannula and the front end portion of said inner cannula prevents the sharply ground front end of the outer cannula from damaging the blood vessel once the double lumen catheter has been inserted therein.

2. A double lumen catheter as set forth in claim 1 wherein said mounting means includes a T-shaped coupling device having a tubular forward end, a tubular rearward end, and a tubular lower end, means within said coupling device defining a guiding aperture tightly surrounding said inner cannula, means securing said outer cannula to the forward end of said coupling device, means connected to the rearward end of said coupling device for conveying inflowing blood to said inner cannula, and means connected to the lower end of said coupling device for conveying outflowing blood from said outer cannula.

3. A double lumen catheter as set forth in claim 2 in which the rearward end of said coupling device includes a tapered guiding sleeve, and wherein said means connected to the rearward end of said coupling device includes a coupling part having said inner cannula fixed thereto, said coupling part including a tapered end adapted to seat within said guiding sleeve to locate said inner cannula in said extended operative position.

4. A double lumen catheter as set forth in claim 3 in which said coupling part has an outwardly extending flange for manual manipulation thereof.

5. A double lumen catheter as set forth in claim 2 wherein the rear end of said outer cannula is beveled and faces the longitudinal axis of the lower end of said coupling device.

6. A double lumen catheter as set forth in claim 2 wherein the inclined front end of the outer cannula forms an opening facing parallel to the longitudinal axis of the lower end of said coupling device.

7. A double lumen catheter as set forth in claim 2 wherein the inclined front end of the outer cannula forms an opening facing perpendicular to the longitudinal axis of the lower end of said coupling device.

8. A double lumen catheter as set forth in claim 1 wherein the front face of the inner cannula is disposed generally perpendicularly with respect to the longitudinal cannula axes.

* * * * *